(12) United States Patent
Naito et al.

(10) Patent No.: US 9,097,697 B2
(45) Date of Patent: Aug. 4, 2015

(54) METHOD FOR SIMULATING DEFORMATION OF RUBBER COMPOUND

(75) Inventors: Masato Naito, Kobe (JP); Wakana Ito, Kobe (JP)

(73) Assignee: Sumitomo Rubber Industries, Ltd., Kobe-shi (JP)

( * ) Notice: Subject to any disclaimer, the term of this patent is extended or adjusted under 35 U.S.C. 154(b) by 441 days.

(21) Appl. No.: 13/553,852

(22) Filed: Jul. 20, 2012

(65) Prior Publication Data

US 2013/0066606 A1  Mar. 14, 2013

(30) Foreign Application Priority Data

Sep. 14, 2011  (JP) ................. 2011-200984

(51) Int. Cl.
  *G06F 7/60*  (2006.01)
  *G01N 33/44*  (2006.01)

(52) U.S. Cl.
  CPC ..................... *G01N 33/44* (2013.01)

(58) Field of Classification Search
  None
  See application file for complete search history.

(56) References Cited

U.S. PATENT DOCUMENTS

| 4,038,543 | A * | 7/1977 | Krisch et al. .............. 250/307 |
| 7,292,966 | B2 * | 11/2007 | Naito .............................. 703/6 |
| 2011/0288838 | A1 * | 11/2011 | Hamatani et al. ............. 703/6 |
| 2012/0232848 | A1 * | 9/2012 | Naito .............................. 703/1 |
| 2012/0323540 | A1 * | 12/2012 | Naito .............................. 703/2 |
| 2013/0051656 | A1 * | 2/2013 | Ito et al. ...................... 382/154 |

FOREIGN PATENT DOCUMENTS

| EP | 1 526 468 A2 | 4/2005 |
| EP | 1 796 130 A1 | 6/2007 |
| JP | 3668238 B2 | 7/2005 |
| JP | 2010-205165 A | 9/2010 |
| WO | WO 00/73092 A1 | 12/2000 |
| WO | WO 2011/145621 A1 | 6/2007 |
| WO | WO 2010/090295 A1 | 8/2010 |

OTHER PUBLICATIONS

FEI Company, "TecnaiTM G2 F30 the benchmark for high performance nanoanalysis", download from http://www.emc.missouri.edu/pdf/2007_07_TecnaiF2_30_ds.pdf, 2007, 2 pages.*
Loos et al., "Electron Tomography on Micrometer—Thick Specimens with Nanometer Resolution", Nano Letters, vol. 9, No. 4, Apr. 2009, pp. 1704-1708.*

(Continued)

*Primary Examiner* — Omar Fernandez Rivas
*Assistant Examiner* — Herng-Der Day
(74) *Attorney, Agent, or Firm* — Birch, Stewart, Kolasch & Birch, LLP

(57) ABSTRACT

A method for simulating deformation of rubber compound including silica particles and an interfacial coupling agent therefor is disclosed. Using a scanning transmission electron microscope (STEM), data of STEM images of the rubber compound are acquired. Based on the STEM image data, a dataset of a 3D structure of the rubber compound is reconstructed. Based on the dataset, a model of the rubber compound is generated. Using the model on which conditions are defined, a deformation calculation is made and a physical quantity is acquired. The rubber compound model comprises a rubber component model, silica particle models and interface models surrounding the silica particle models and defined as being harder than the rubber component model.

5 Claims, 15 Drawing Sheets

(56) References Cited

OTHER PUBLICATIONS

Besser et al., "FEI Tecnai F-20 Operations Manual", Portland State University, Center for Electron Microscopy and Nanofabrication, Jun. 2010.*

Dohi et al: "Heterogeneity of a vulcanized rubber by the formation of ZnS clusters", Polymer, Elsevier Science Publishers B.V, GB vol. 48, No. 9, Apr. 14, 2007; pp. 2526-2530; XP022043329.

* cited by examiner

722nm × 1191nm × 500nm

METHOD FOR SIMULATING DEFORMATION OF RUBBER COMPOUND

BACKGROUND OF THE INVENTION

The present invention relates to a computerized method for simulating deformation of rubber compound comprising a rubber component, silica particles and an interfacial coupling agent, more particularly to a method for generating a finite element model of the rubber compound capable of accurately simulating the deformation.

Conventionally, rubber compounds used in various industrial products, e.g. tires, sports goods and the like contain carbon black as a reinforcing filler to improve mechanical characteristics.

In recent years, on the other hand, silica becomes widely used instead of carbon black for the following reasons. Generally, an energy loss in a silica-rich compound is less in comparison with a carbon-rich compound, therefore, by using a silica-rich compound as the tread rubber of a tire, the rolling resistance can be decreased which contributes to lessen the fuel consumption of the vehicle. Further, silica is a non-petroleum resource, therefore to use silica as reinforcing fillers is environmentally-friendly.

Thus, in view of research and development of vehicle tires, it is very beneficial to accurately simulate deformations of a rubber compound containing silica as reinforcing filler particles.

Computerized methods for simulating deformation of rubber compound are disclosed in Japanese patent No. 3668238 and the following non-patent document.

"A three-dimensional constitutive model for the large stretch behavior of rubber elastic materials" Authors: Ellen M. Arruda and Marry C. Boyce, Publication: Journal of the Mechanics and Physics of Solids, vol. 41, issue 2, Pages 389-412, Publication Date February 1993

In Japanese patent No. 3668238, the finite element model of a rubber compound includes a rubber component model and a filler particle model, and by the use of a finite element method, a deformation calculation is made taking account of influence of the filler.

Therefore, in the case of a silica-rich rubber compound, used is a rubber compound model including a rubber component model and silica particle models. And in order to make a deformation calculation, on the silica particle models, physical properties, e.g. elastic modulus as a hard elastic body are defined. On the rubber component model, physical properties, e.g. relationship between stress and elongation as a viscoelastic body is defined.

However, if a deformation simulation is made by applying strain e.g. tensile deformation to such rubber compound model, simulation results are not always coincide with actual phenomena although in the case of a carbon-rich rubber compound simulation results are well coincide with actual phenomena.

Therefore, the present inventors studied the differences between simulation results and actual phenomena and found that such difference is caused by an interfacial coupling agent added in a silica-rich rubber compound.

SUMMARY OF THE INVENTION

It is therefore, an object of the present invention to provide a method for simulating deformation of a rubber compound comprising a rubber component, silica particles and an interfacial coupling agent, in which accurate deformation calculations and simulations are possible.

According to the present invention, a method for simulating deformation of rubber compound including a rubber component, silica particles and an interfacial coupling agent for coupling the silica particles with the rubber component, comprises:

a STEM image acquiring step in which, by the use of a scanning transmission electron microscope (STEM), data of STEM images of the rubber compound are acquired;

a three-dimensional structure reconstruction step in which, based on the data of the STEM images, a dataset of a three-dimensional structure of the rubber compound is reconstructed;

a finite element model generating step in which, based on the dataset of the three-dimensional structure of the rubber compound, a finite element model of the rubber compound is generated;

a deformation calculation step in which a deformation calculation is made by the use of the finite element model of the rubber compound on which conditions are defined; and a step of in which a physical quantity is acquired through the deformation calculation, wherein the finite element model generating step comprises:

reconstructing data of a slice image of the rubber compound from the dataset of the three-dimensional structure;

identifying a domain of the rubber component and domains of the silica particles in the slice image through an image processing of the slice image; and generating the finite element model of the rubber compound, wherein the generating of the finite element model comprises:

creating silica particle models by subdividing the domains of the silica particles into finite elements;

creating an interface model made up of finite elements surrounding each of the silica particle models;

creating a rubber component model by subdividing the domain of the rubber component into finite elements; and defining a physical property on the finite elements of the interface models as being harder than the rubber component.

Preferably, in the STEM image acquiring step, the focal point of the scanning transmission electron microscope is set in a thickness center region of a specimen of the rubber compound. The STEM images are took at different tilt angles of the specimen of the rubber compound while the focal point of the scanning transmission electron microscope is set in a thickness center region of the specimen of the rubber compound based on an apparent thickness measured along the direction of the electron beam axis across the specimen of the rubber compound. Preferably, the thickness of the specimen of the rubber compound is 200 to 1500 nm. The distance between the specimen of the rubber compound and a detector for the transmission electrons of the scanning transmission electron microscope is 8 to 150 cm. The finite element model generating step preferably includes a step in which a first unvulcanized rubber compound having the same composition as that of said rubber compound as the analysis object and a second unvulcanized rubber compound having a composition same as the first unvulcanized rubber compound except that the interfacial coupling agent is eliminated are prepared, a step in which each of the first and second unvulcanized rubber compounds is immersed in solvent to remove the rubber component and thereby to obtain residue, a step in which the difference between a peak temperature T1 of the loss tangent of the residue of the first unvulcanized rubber compound and a peak temperature T2 of the loss tangent of the residue of the second unvulcanized rubber compound is determined, a step in which a basic vulcanized rubber compound having a composition same as the first unvulcanized rubber compound except that the silica particles are eliminated, and plural kinds of vulcanized rubber compounds which are the same as the basic vulcanized rubber compound but different in the crosslink density from each other and from the basic vulcanized rubber compound, are prepared, a step in which a peak temperature of the loss tangent of each of vulcanized rubber compounds, which are the basic vulcanized rubber compound and said plural kinds of vulcanized rubber compounds, is measured, a step in which a relationship between the peak temperature of the loss tangent of the vulcanized rubber compounds and the crosslink density is obtained, a step in which, from the obtained relationship, the crosslink density when the peak temperature of the loss tangent is equal to the sum of the difference |T2−T1| and the peak temperature T3 of the loss tangent of the basic vulcanized rubber compound is found, a step in which a physical property of a vulcanized rubber compound having the found crosslink density is measured and defined for the interface model.

In the present invention, therefore, an accurate finite element model based on the actual rubber compound can be generated. By making deformation calculations using such model, accurate simulation results can be obtained. Further, since the finite element model include the interface models, it is possible to obtain calculation results having high correlation with the deformational behavior of the actual rubber compound.

Further, by setting the focal point in a thickness center region of the specimen, the range on the specimen in which a clear image can be obtained becomes increased, and thereby it becomes possible to obtain the rubber compound model in which the dispersion of the silica particles is more accurately simulated.

BRIEF DESCRIPTION OF THE DRAWINGS

FIGS. 12(a) and 12(b) are exemplary graphs used in order to determine physical properties to be defined for the interface model, wherein FIG. 12(a) shows an example of the relationship between the peak temperature of loss tangent of a residue and the content of the interfacial coupling agent therein, and FIG. 12(b) shows an example of the relationship between the crosslink density (or sulfur content) and the peak temperature of loss tangent of a vulcanized rubber compound without silica.

DESCRIPTION OF THE PREFERRED EMBODIMENTS

Embodiments of the present invention will now be described in detail in conjunction with accompanying drawings.

Figure 3:
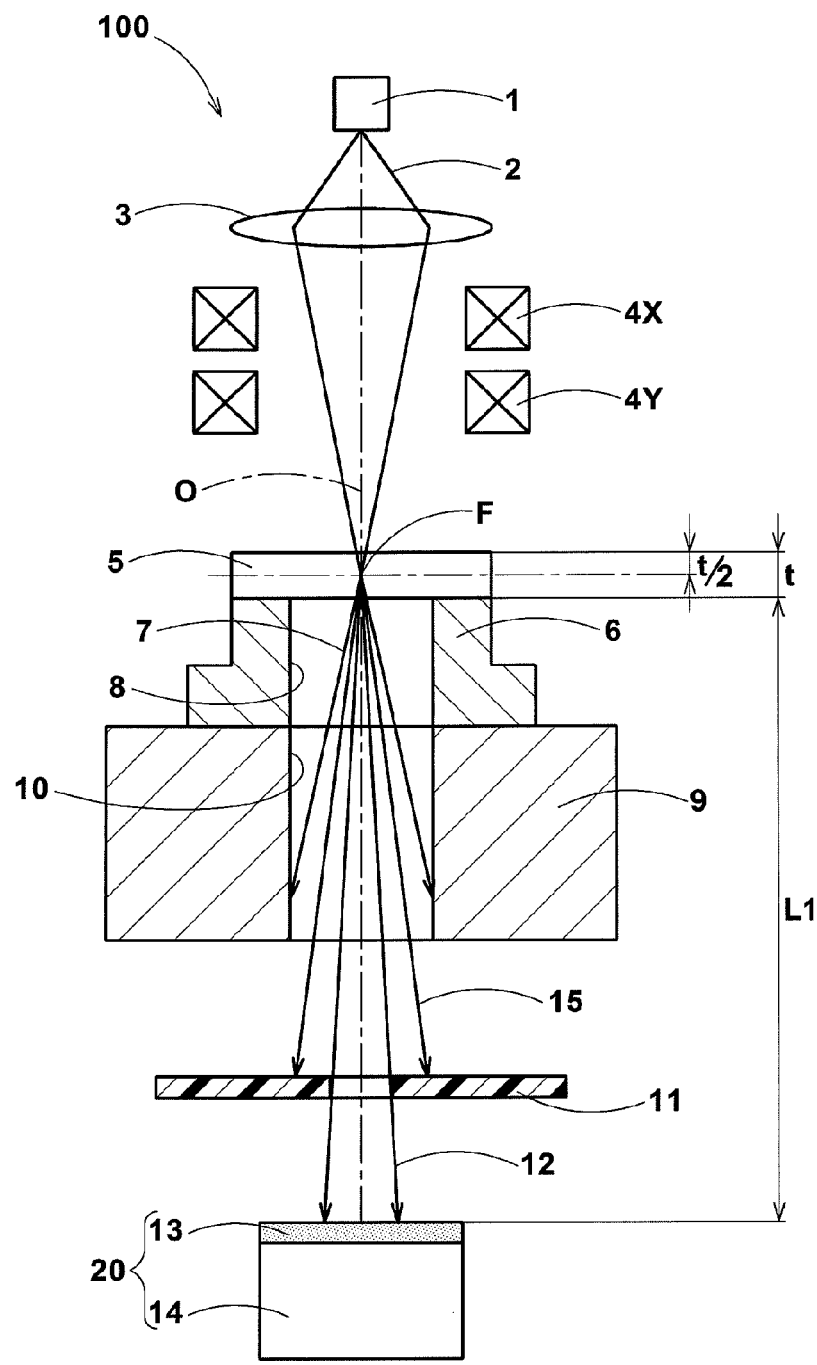
FIG. 3 is a diagram showing a scanning transmission electron microscope used in the method according to the present invention.

In the present invention, a two-dimensional or three-dimensional finite element model of a rubber compound (c) is generated by the use of a scanning transmission electron microscope 100 shown in FIG. 3 and a computer (not shown). Then, using the computer, a simulation of deformation of the rubber compound is carried out by making deformation calculations on the finite element model in order to analyze the rubber compound (c).

Scanning Transmission Electron Microscope

As usual, the scanning transmission electron microscope (STEM) 100 comprises: an electron gun 1 directed perpendicularly to a horizontal plane and capable of emitting electrons downward; a focusing lens 3 for focusing the electrons as an electron beam 2 on a specimen 5 of the rubber compound (c); scanning coils 4 including an X-direction scanning coil 4X and a Y-direction scanning coil 4Y for deflecting the electron beam 2 in the X-direction and Y-direction to scan the specimen 5; a specimen holder 6 for holding the specimen 5; and a specimen stage 9 on which the specimen holder 6 is detachably fixed. In a central portion of the specimen holder 6, an electron beam pass-through hole 8 is formed along the central axis (O) of the scanning transmission electron microscope 100 so that transmission electrons 7 which penetrate through the specimen 5 can pass through the hole 8.

In a central portion of the specimen stage 9, an electron beam pass-through hole 10 is formed along the central axis (O) and continuously from the electron beam pass-through hole 8 so that the transmission electrons 7 can pass through the hole 10. The microscope 100 further provided on the downstream side of the specimen stage 9 with a scattering angle limiting aperture 11 in order to limit the passing-through of the transmission electrons 7.

Further, on the downstream side of the scattering angle limiting aperture 11, there is disposed a detector 20 for the transmission electrons 15 passing through the aperture 11. The detector 20 comprises a scintillator 13 and a photoelectron multiplier tube 14.

The scintillator 13 reemits the energy of the incident electrons 12 passing though the aperture 11, in the form of light.

The photoelectron multiplier tube 14 converts the incident light from the scintillator 13 to an electronic signal.

Incidentally, the above-mentioned specimen stage 9, scattering angle limiting aperture 11, scintillator 13 and photoelectron multiplier tube 14 are arranged in a specimen room of a casing main body (not shown) of the microscope system 100.

Rubber Compound as Analysis Object

Figure 1:
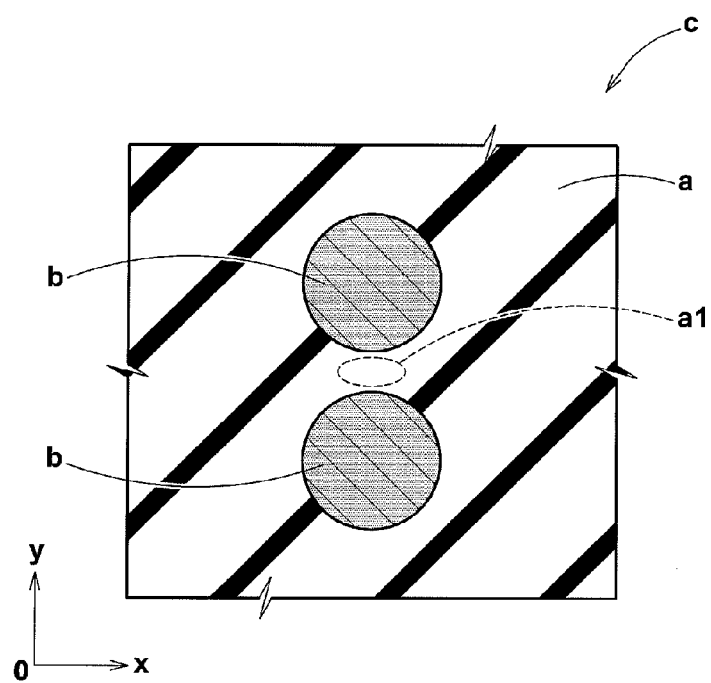
FIG. 1 is a microscopical cross sectional view of a simplified example of a rubber compound.

In the present invention, the analysis object to be simulated and analyzes is a rubber compound (c) which comprises as schematically shown in FIG. 1, a rubber component (a) as the matrix rubber, silica particles (b) as reinforcing filler dispersed in the matrix rubber, and an interfacial coupling agent for coupling the silica particles with the rubber component.

The rubber component (a) can be, for example, natural rubber (NR), isoprene rubber (IR), butyl rubber (IIR), butadiene rubber (BR), styrene butadiene rubber (SBR), styrene isoprene butadiene rubber (SIBR), ethylene-propylene-diene rubber (EPDM), chloroprene rubber (CR), acrylonitrile butadiene rubber (NBR) and the like.

The interfacial coupling agent can be, for example, a silane coupling agent. As the silane coupling agent, for example, Bis[2-(triethoxysilyl)ethyl]polysulfide,
Bis[3-(triethoxysilyl)propyl]polysulfide,
Bis[3-(triethoxysilyl)propyl]disulfide,
Bis[4-(triethoxysilyl)butyl]polysulfide,
Bis[2-(trimethoxysilyl)ethyl]polysulfide,
Bis[3-(trimethoxysilyl)propyl]polysulfide,
Bis[4-(trimethoxysilyl)butyl]polysulfide
and the like can be used alone or in combination.

Of course the rubber component (a) and coupling agent are not limited to these examples.

Further, in the rubber compound (c), various additives, e.g. sulfur, vulcanization accelerator and the like may be added.

In this embodiment, a slice of the rubber compound having a constant thickness (t) is used as the above-mentioned specimen 5.

Method for Simulating Deformation of Rubber Compound

Figure 2:
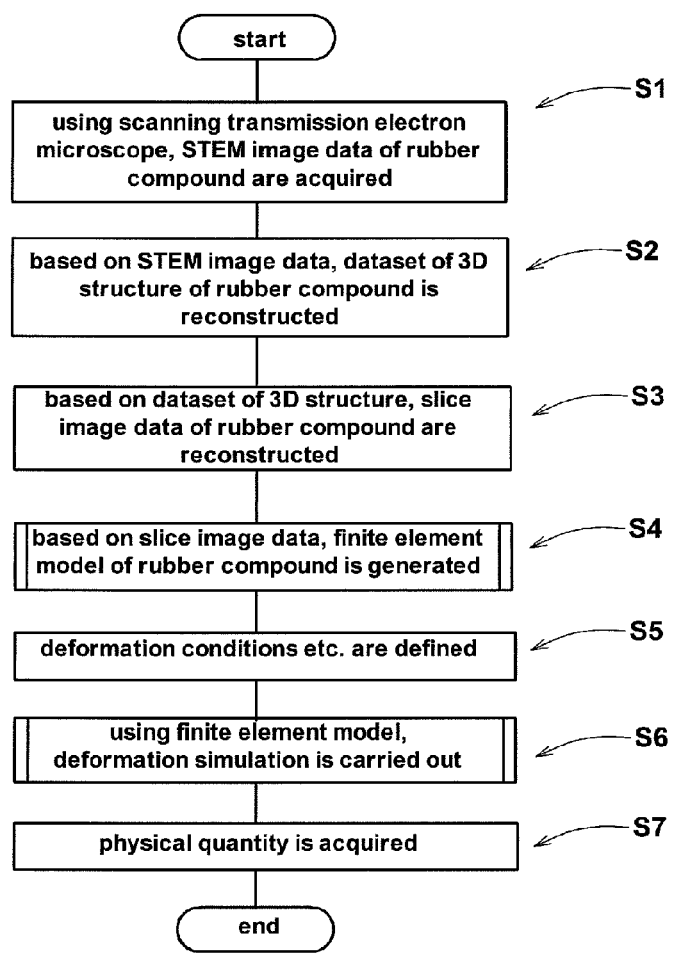
FIG. 2 is a flow chart for explaining a method for simulating deformation of rubber compound as an embodiment of the present invention.

A flow chart implementing the simulating method as an embodiment of the present invention is shown in FIG. 2. This method comprises the following steps.

STEM Image Acquiring Step S1

In this step S1, by the use of the scanning transmission electron microscope (STEM) 100, STEM images of the rubber compound (c) are acquired.

Incidentally, the specimen holder 6 with the specimen 5 is attached to the specimen stage 9 by an operating personnel. The electron beam 2 emitted from the electron gun 1 and accelerated by an accelerator (not shown) and focused by the focusing lens 3 is scanned on the specimen 5 by the X-direction and Y-direction scanning coils 4X and 4Y.

The electrons 7, which penetrate through the specimen 5 with or without scattered, go out from the lower surface of the specimen 5. The outgoing electrons 7 travel through the holes 8 and 10 to the scattering angle limiting aperture 11 which allows the electrons having particular scattering angles to pass through it. The electrons 12 passing through the scattering angle limiting aperture 11 go into the scintillator 13, and thereby the energy of the incident electrons 12 is reemitted in the form of light. Then by the accompanying photoelectron multiplier tube 14, the light is converted to an electronic signal.

The electrical signal is amplified and converted to digital data by an amplifier and A/D converter (not shown).

The digital data are transmitted to a display (not shown) in which, according to the transmitted signal, brightness modulation is made, and an electron beam transmission image reflecting the internal structure of the specimen 5 is displayed as a STEM image, and at the same time, the digital data are stored in a memory of the computer.

Thus, a plurality of STEM images corresponding to the scan positions are acquired as the STEM images' dataset.

The intensity and scattering angle of the outgoing electrons 7 are varied depending on the internal state, thickness and/or atomic species of the specimen 5.

The scattering angle is also varied by the accelerating voltage. For example, if the accelerating voltage is decreased, the electrons are scattered more in the specimen 5, and the scattering angle or outgoing angle from the lower surface of the specimen 5 with respect to the central axis (O) is increased.

Figure 4:
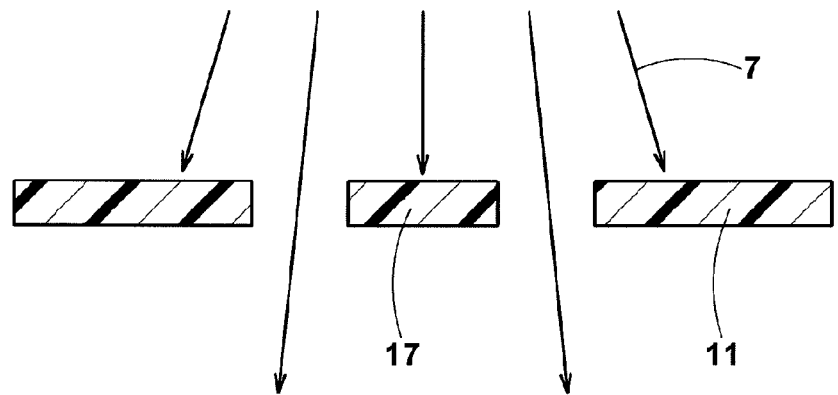
FIG. 4 is a diagram showing a scattering angle limiting aperture for dark-field image.

As shown in FIG. 4, the scattering angle limiting aperture 11 may be provided in its center with a masking shield 17 for further limiting the passing of the electrons 7 although the example shown in FIG. 3 is not provided with such masking shield. In general, the electron beam transmission image becomes a bright-field image when the additional masking shield is not used, but it becomes a dark-field image if the masking shield is used.

In order to create a clear image, the camera length L1 namely the distance between the specimen 5 and the scintillator 13 is preferably set in a range of from 8 to 150 cm.

The accelerating voltage for the electron beam may be set in a range of 100 to 3000 kV depending on the specimen 5.

In the STEM image acquiring step S1 in this embodiment, a plurality of images of the rubber compound (c) are took from different angles with respect to the central axis (O) of the scanning transmission electron microscope 100.

For this purpose, the microscope 100 is provided with a specimen tilting device (not shown) to tilt the specimen 5 with respect to the central axis (O).

Figure 5:
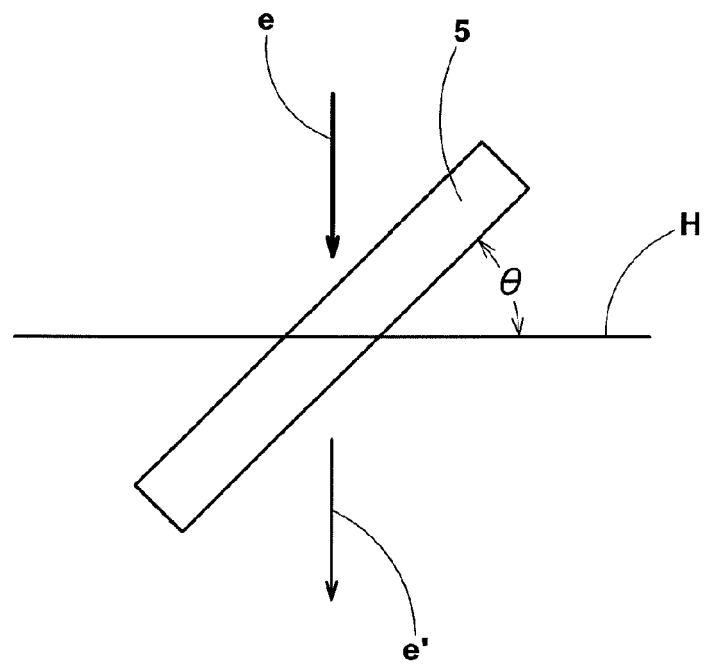
FIG. 5 is a diagram for explaining a device for tilting the specimen.

With this, as shown in FIG. 5, the specimen 5 can be held at different tilt angles θ with respect to a horizontal plane H. In this embodiment, the computer outputs a control signal to the specimen tilting device and according thereto the device tilts the specimen 5 at a specific angle θ.

The variable range of the angle θ of the specimen 5 is −90 to +90 degrees, preferably −70 to +70 degrees. However, if the specimen is a round bar of the rubber compound, the variable range of the angle θ may be −180 to +180 degrees.

Firstly, the specimen 5 is tilted at a measuring start angle θ and in this tilted state, the STEM images or the dataset thereof are acquired as explained above.

Then, until a measuring stop angle θ, the process of changing the tilt angle of the specimen 5 and acquiring the dataset of the STEM images of the specimen 5 at that tilt angle are repeated at a step in a range of from 0.5 to 4 degrees, preferably 1 to 2 degrees in order to obtain the after-mentioned slice images clearly and efficiently.

Thereby, the dataset of the STEM images of the specimen inclined at different tilt angles are obtained.

Incidentally, the measuring start angle θ and measuring stop angle θ can be arbitrarily set on the microscope by using a controller. In this embodiment, the measuring start angle θ is +70 degrees, and the measuring stop angle θ is −70 degrees.

Figure 7:
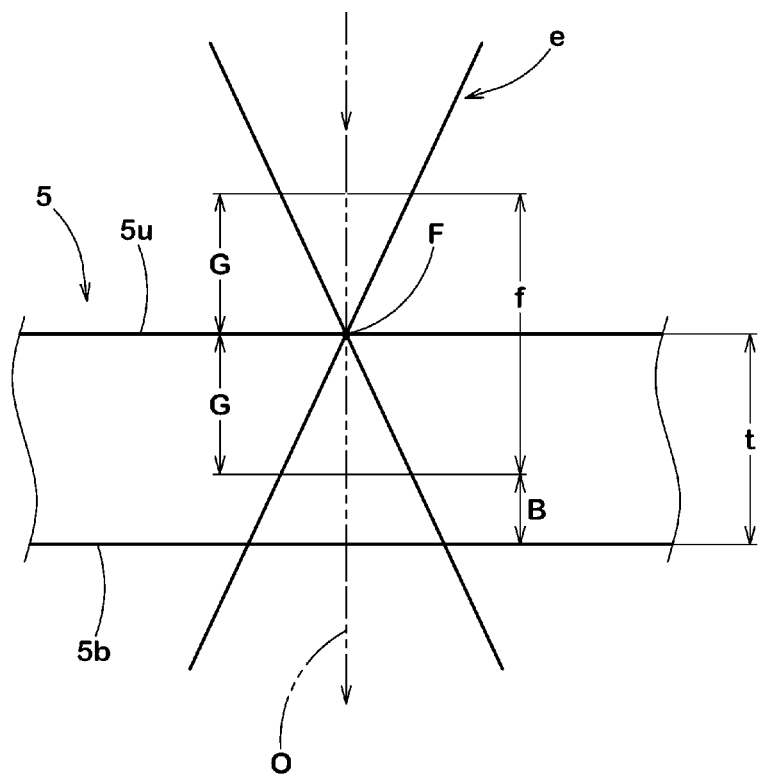
FIG. 7 is a schematic sectional view for explaining relationships among the depth of field of a scanning transmission electron microscope, a position of the focal point of the microscope, and the thickness of a specimen.

Conventionally, the focal point F of the electron beam (e) is set at the upper surface 5u of the specimen 5. In this case, there is a possibility that a clear image cannot be obtained in the vicinity of the lower surface 5b of the specimen 5. For instance, as shown in FIG. 7, if the thickness (t) of the specimen 5 is 1000 nm, the depth (f) of field of the microscope is 1200 nm (or +/−600 nm), and the focal point F is set at the surface 5u of the specimen 5, then a lower part B having 400 nm thickness of the specimen 5 is outside the depth of field, and accordingly, a clear image of such part B can not be obtained. This problem is liable to occur with increase in the thickness (t).

Figure 6A:
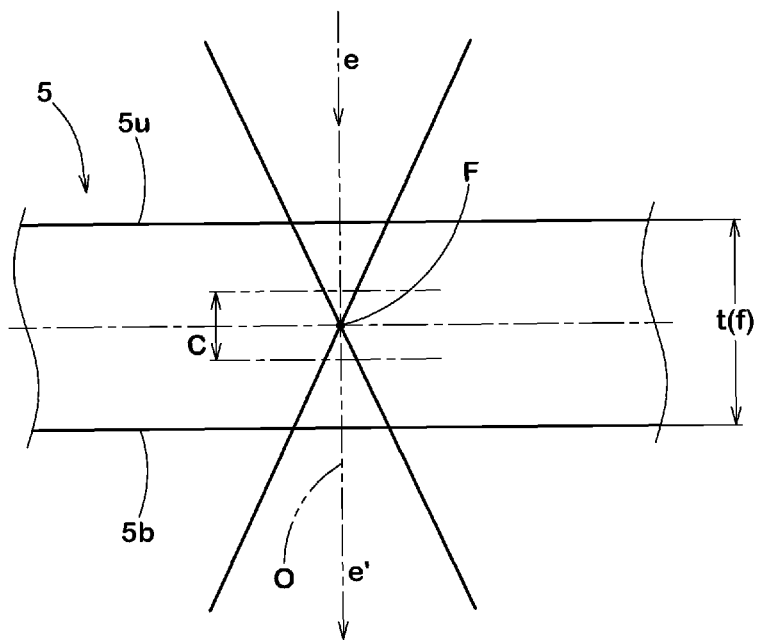
FIG. 6(a) is a schematic sectional view of the specimen for explaining the position of the focal point, taken along a section including the electron beam axis which is perpendicular to the incidence plane.

In this embodiment, therefore, the focal point F of the electron beam (e) is set in a thickness center region C of the specimen 5 as shown in FIG. 6(a). Thereby, the range on the specimen 5 in which a clear image can be obtained becomes increased. It is desirable that the depth (f) of field can completely overlaps or encompass the thickness (t) of the specimen 5.

In FIG. 6(a), the upper surface 5u and the lower surface 5b of the specimen 5 are perpendicular to the electron beam axis (namely, the incidence angle is equal to 90 deg.).

Figure 6B:
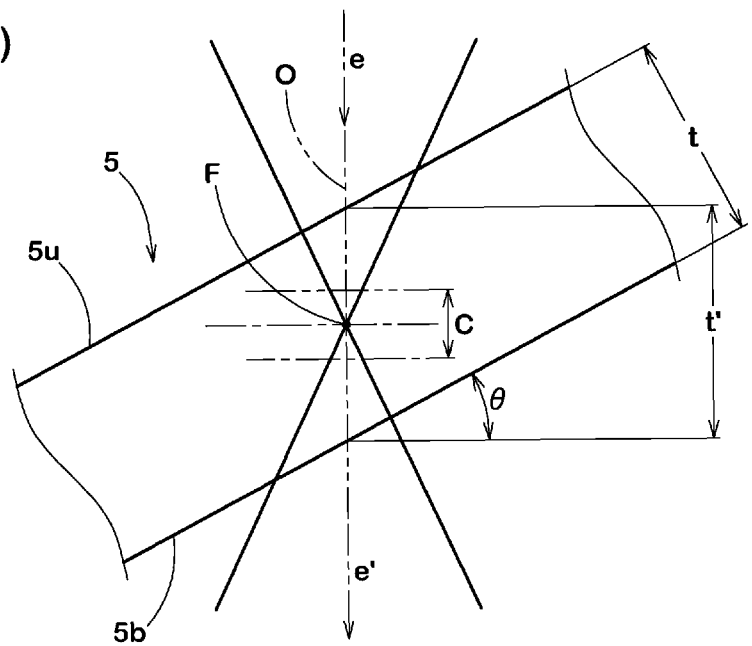
FIG. 6(b) is a schematic sectional view of the specimen for explaining the position of the focal point, taken along a section including the electron beam axis which inclines with respect to the incidence plane.

In FIG. 6(b), the upper surface 5u and the lower surface 5b of the specimen 5 are inclined with respect to the electron beam axis (namely, the incidence angle is not equal to 90 deg.). Under such inclined state, the thickness of the specimen 5 measured along the electron beam axis is referred to as apparent thickness (t') in contrast to the real thickness (t) measured perpendicularly to the upper surface 5u.

From the real thickness (t) and the incidence angle, the apparent thickness can be obtained as follows apparent thickness(t')=real thickness(t)/sin(incidence angle).

It is desirable that the thickness central region C within which the focal point F is set, ranges 30%, preferably 20%, more preferably 10% of the real/apparent thickness. The thickness central region C may be off-centered, but preferably it is centered on the center of the real/apparent thickness.

The real thickness (t) may be less than 200 nm as usual, but it is preferably set in a range of from 200 to 1500 nm, more preferably 500 to 1000 nm. By increasing the thickness (t) near to 1500 nm, the dispersion of the silica particles including a compact cluster having a diameter of 200 nm or more can be accurately simulated.

Incidentally, the focal point F is adjusted by the focusing lens 3 and/or specimen stage 9 by the use of a focal point adjuster of the microscope system 100.

Three-Dimensional Structure Reconstruction Step S2

In this step S2, from the dataset of the STEM images acquired in the step S1, a three-dimensional structure of the rubber compound containing silica is reconstructed as numerical data (hereinafter the "3D dataset") by executing a tomographic method with the computer, and the 3D dataset is stored in a memory of the computer.

Thus, the reconstructed 3D dataset of the three-dimensional structure includes data of the silica particles dispersed in the rubber compound.

As to the dataset of the STEM images, those acquired by changing the tilt angle of the specimen 5 as explained above can be preferably used. But, it is also possible to use those acquired by not changing the tilt angle, namely acquired at a single tilt angle of the specimen 5 preferably zero degree with respect to the central axis (O) of the microscope 100.

From the 3D dataset, the computer can create and output various images as visual information as well as numerical data.

Figure 8:
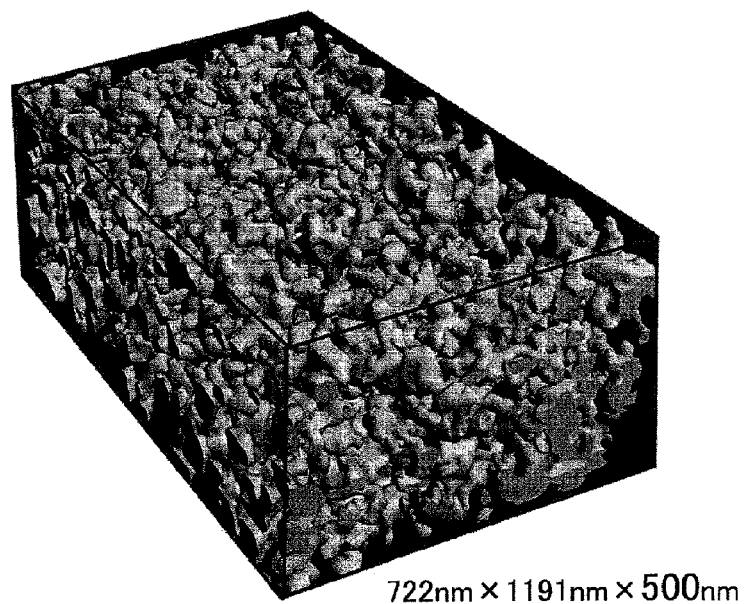
FIG. 8 is a perspective view produced from a dataset of the three-dimensional structure of a rubber compound.

FIG. 8 shows such created image which is a perspective view of the silica particles dispersed in the rubber compound.

Slice Image Acquiring Step S3

In this step S3, from the 3D dataset of the three-dimensional structure of the rubber compound, slice images of the rubber compound (c) taken along predetermined sections of the rubber compound (c) are reconstructed by the computer as numerical data (herein after the "slice image dataset"), and the slice image dataset is stored in a memory of the computer. The above-mentioned predetermined sections of the rubber compound can be arbitrarily determined according to the coordinate system (Cartesian or polar or cylindrical) employed in the subsequent modeling step S4.

Finite Element Model Generating Step S4

This step S4 is to generate a finite element model of the rubber compound from the slice image dataset.

Firstly, the slice image is subjected to an image processing to divide the entire region of the slice image into a domain of the rubber component (a), domains of the silica particles (b) and/or a domain of other component if any.

As to the image processing, a known method can be used in which, based on threshold levels of gray level, micro regions of the slice image are each identified whether it is a rubber component domain or a silica particle domain (or other domain if any).

Then, a grid (e.g. structured grid) is defined and superimposed onto the image-processed slice image or images. And, for each element (e.g. quadrilateral element, hexahedral element or the like) of the grid, it is computed which one of the rubber component domain, silica particle domain and other domain if any has the highest proportion of area or volume in the concerned element, and the element is defined as being one having the highest proportion.

Namely, the computer determines whether the element belongs to the rubber component or the silica particle or other component if any.

Silica Particle Models 22

By the elements determined as belonging to the silica particles, models 22 of the silica particles are defined.

Interface Model 23

Then, by the use of elements completely surrounding each of the silica particle models 22, an interface model 23 is defined.

The interface model 23 is to simulate the function of the interfacial coupling agent (silane coupling agent) for chemically coupling the silica particle with the rubber component. The interface model 23 is defined as a thin layer whose inner surface abuts on the surface of the silica particle model 22 and which completely covers the surface of the silica particle model 22. The outer surface of the interface model 23 abuts on the rubber component model 21 and/or another interface model 23. The interface model 23 has a certain thickness. In the drawings, the thickness corresponds to a dimension of one element. However, according to experimental results, it may be preferred that the thickness of the interface model 23 is in a range of from about 10% to about 30%, more preferably about 15 to about 25% of the diameter of the silica particle model 22.

Further, such a boundary condition that the inner surface of the interface model 23 does not separate from the surface of the silica particle model 22 is defined for the interface model 23. However, if needed, it is possible to define such a boundary condition that when the stress increases over a predetermined value, they are separated from each other.

Rubber Component Model 21

By the elements determined as belonging to the rubber component, but excluding those assigned to the interface models 23, a model 21 of the rubber component is defined.

Finite Element Model 5a of the Rubber Compound

Thus, the finite element model 5a of the rubber compound (c) (hereinafter also referred to as rubber compound model 5a) is defined as being composed of the rubber component model 21, the silica particle models 22 and the interface models 23 surrounding the silica particle models 22.
In the rubber component model 21, the rubber component (a) is as usual discretized into a finite number of elements eb.
In the silica particle models 22, the silica particle (b) is as usual discretized into a finite number of elements eb.
As explained, since the grid generation is based on the slice image or images accurately created from the 3D dataset of the rubber compound, it is possible to obtain a precise finite element model of the rubber compound in which the dispersion of the silica particles is accurately reproduced in the rubber compound model.

Kinds of Models and Elements

According to the present invention, the finite element model 5a can be two-dimensional or three-dimensional. For example, if only a plane strain problem is to be solved through the after-mentioned deformation simulation, a two-dimensional finite element model 5a may be sufficient.

Figure 9:
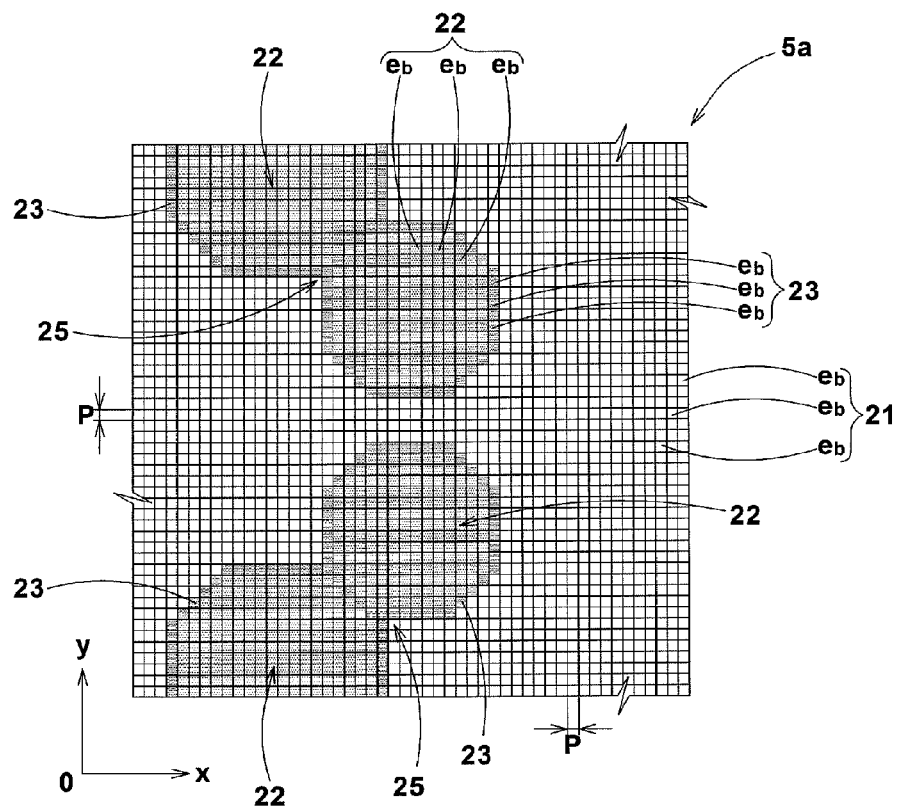
FIG. 9 is a diagram showing a small part of a finite element model of a simplified example of a rubber compound.

FIG. 9 shows a microscopical region of a simplified example of the rubber compound model 5a, wherein the shaded areas indicate the silica particle models 22 and interface models 23. In this example, as shown, the rubber compound model 5a is a structured grid model made up of square elements (eb) having boundary GD (L1 and L2) at even intervals P in the x-axis direction and y-axis direction (therefore, this example is two-dimensional).
However, the kind of the element is not always limited to this example. Various kinds of elements, e.g. triangular elements, other kinds of quadrilateral elements and the like can be used.

Regardless of whether 2D or 3D, by employing a structured grid model, it is possible to generate the rubber compound model 5a rapidly.

In this finite element model generating step S4, information which is required for the deformation simulations or numerical analyses conducted by the use of a numerical analysis method, e.g. a finite element method or the like is defined for the elements eb.
On each element eb, material characteristics or properties (density, elastic modulus and the like) of the part of the rubber compound which part is represented by the concerned element are defined. Specifically, on each of the elements eb of the rubber component model 21, silica particle models 22 and interface models 23, material constants corresponding to physical properties of the rubber component, the silica particle and the interface therebetween are defined and stored in a memory of the computer as numerical data.
The information also includes indexes and coordinate values of node points (n) of each element eb.

In comparison with the rubber component, the silica particle is very hard. Therefore, the silica particle is treated as an elastic body whereas the rubber component is treated as an a viscoelastic body.

Accordingly, the silica particle model 22 is provided with physical properties as an elastic body corresponding to the silica particle.

The rubber component model 21 is provided with physical properties as a viscoelastic body corresponding to the rubber component. For example, a function expressing the relationship between stress and elongation of the rubber component is defined for the elements constituting the rubber component model 21.

Figure 10:
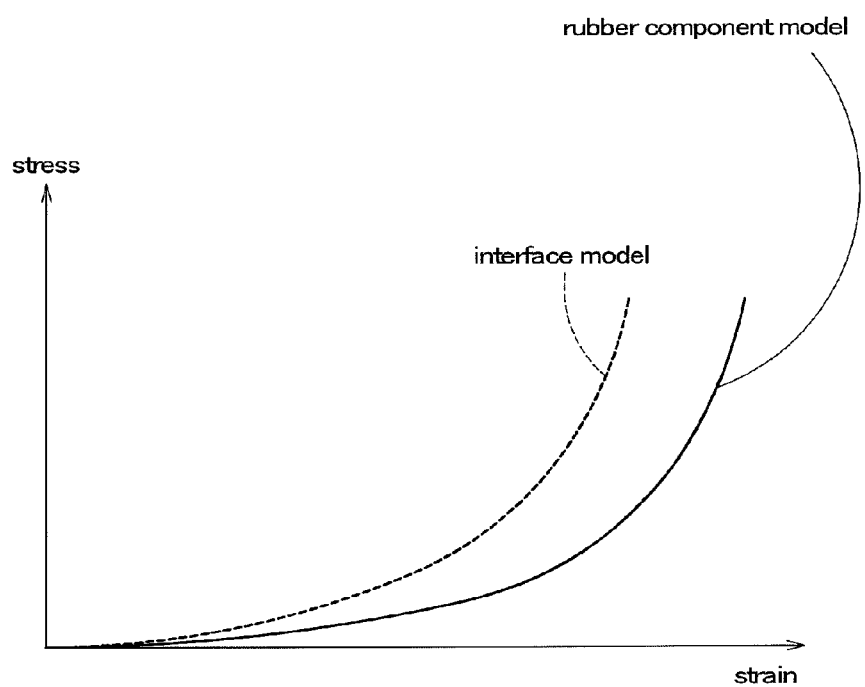
FIG. 10 is a diagram showing examples of the stress-strain curves defined for the rubber component model and interface model as a physical property.

The interface model 23 is provided with at least such a physical property that it is harder than the rubber component. As a result, the interface model 23 is defined as being hard to elongate in comparison with the rubber component model 21 as shown in FIG. 10.

In the actual rubber compound, the interfacial coupling agent also exists in between the silica particles not only the neighborhood of the surfaces of the silica particles. Therefore, the crosslink density in the in-between part becomes higher than that of the rubber component only, namely, rubber component without the interfacial coupling agent.
It is therefore preferable to simulate this state by defining threshold stretch (strain at which stress rises sharply) for the interface model 23 and the rubber component model 21 such that the threshold stretch of the interface model 23 is less than that of the rubber component model 21.

The rubber compound model 5a usually includes a plurality of silica particle models 22 linked by the interface models 23 like a network (hereinafter, the network 25 of silica particle models).
According to observations using the electron microscope, the silica particles in the rubber compound forming such network usually amount to about 30% of the total, and it is inferable that the silica particles are linked by a condensation reaction of the interfacial coupling agent.

By the way, the interfacial coupling agent causing the condensation reaction functions as a cross-linking agent, therefore, the crosslink density is increased in the neighborhood of the silica particles. Thus, by the above-mentioned network structure, the distances between the silica particles are maintained relatively short, which becomes a resistance to deformation of the rubber compound. As a result, the rubber compound becomes further stiffened in cooperation with the reinforcing effect of the silica particles themselves.

Figure 11:
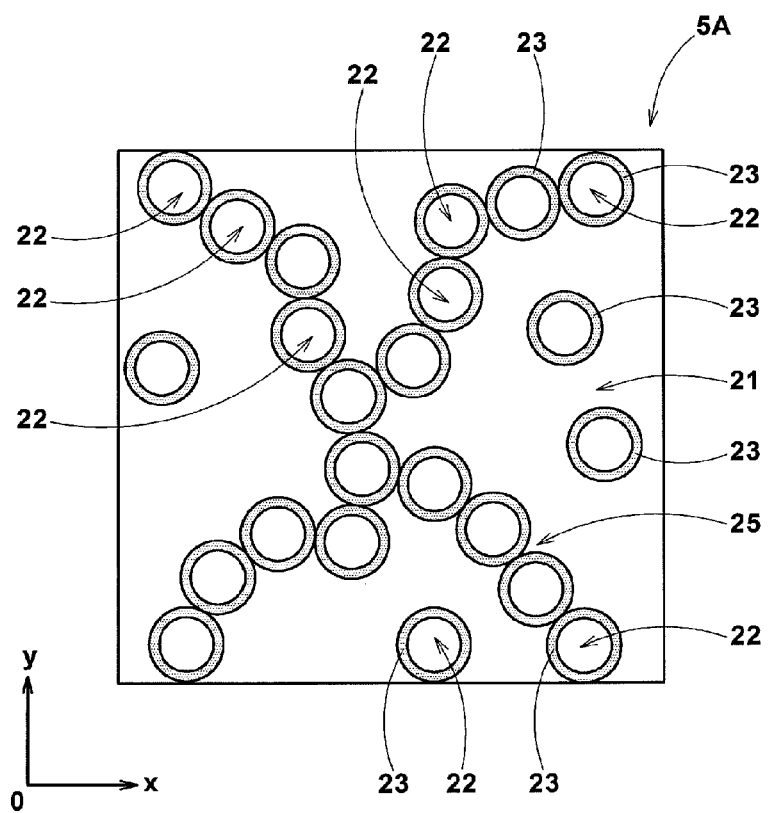
FIG. 11 is a diagram showing a rubber compound model for explaining mutually linked silica particle models.

FIG. 11 schematically shows a microscopic structure 5A of the rubber compound model 5a, wherein some of the silica particle models 22 are mutually linked forming a network 25. In this example, the network 25 extends over the almost entire region of the rubber compound model 5a.

Considering the microscopic structure 5A used in the after-mentioned homogeneization method, it is preferable to adopt such a microscopic structure 5A in which the network 25 extends continuously between the edges of the microscopic structure in a certain direction so that the interface models 23 forming the network 25 and abutting on the edges can link with those in the next microscopic structure in the certain direction. This direction may be x, Y and z-directions in cartesian coordinate system if the rubber compound model 5a is generated as a three-dimensional model based on such coordinate system. When the rubber compound model 5a is generated as a two-dimensional model in a orthogonal coordinate system and if deformation in one direction is to be mainly calculated, the above-mentioned certain direction may be this one direction. For example, if this one direction is Y-axis direction, then the above-mentioned edges on which the interface models 23 abut are the edges in Y-axis direction.

Determination of Physical Properties for Interface Model

The physical properties to be defined on the interface model 23 are difficult to obtain through an experimental measurement, therefore, it is preferable that they are determined by the following particular method.

Firstly, it is assumed that the rubber compound (c) as the analysis object has a composition such that
the content of the silica is #Csil,
the content of the interfacial coupling agent is #Cint, and
the content of the sulfur is #Csul.

If the increase in the peak temperature of the loss tangent of a plain vulcanized rubber compound, whose composition is same as that of the rubber compound (c) except that it does not contain the silica and interfacial coupling agent, when the content of the sulfur is increased from #Csul to a specific value #CsulX becomes equal to the increase in the peak temperature of the loss tangent of the under-mentioned residue, where the sulfur content is #Csul, when the content of the interfacial coupling agent is increased from 0 to #Cint, then physical properties of the plain vulcanized rubber whose sulfur content is the above-mentioned specific value #CsulX are experimentally measured and defined for the interface models.

More specific explanation is given below.

Firstly, first and second unvulcanized rubber compounds are prepared.

The first unvulcanized rubber compound has the rubber composition same as that of the rubber compound (c).

The second unvulcanized rubber compound has a composition same as the first unvulcanized rubber compound except that the interfacial coupling agent is eliminated.

For example, the first unvulcanized rubber compound contains 8 wt % (=#Cint) of the interfacial coupling agent.

It is desirable to prepare plural kinds of unvulcanized rubber compounds in which the content of only the interfacial coupling agent is varied from that of the first unvulcanized rubber compound (#Cint).

Each of the unvulcanized rubber compounds is prepared by uniformly kneading the materials by the use of a banbury mixer.

Next, each of the unvulcanized rubber compounds is immersed in solvent to remove the rubber component and thereby to obtain the above-mentioned residue.

For instance, the unvulcanized rubber compound put in a wire-wove basket (preferably 150 mesh/inch) is immersed in toluene for 48 hours at ambient temperature. As a result, the rubber component is dissolved in the solvent.

Thereby, from the first unvulcanized rubber compound, the first residue including the silica, interfacial coupling agent, sulfur and other additives is obtained in the basket.

From the second unvulcanized rubber compound, the second residue including the silica, sulfur and other additives (the interfacial coupling agent is not contained) is obtained in the basket.

Incidentally, if the vulcanized rubber compound is used instead of the unvulcanized rubber compound, the rubber component is hard to dissolve in the solvent.

Since the residue does not contain the rubber component in substance, the first residue can be considered as an equivalent to the combination of the silica particle models 22 and interface models 23 obtain by removing the rubber component model 21 from the rubber compound model 5a.

The residue is solidified by pressing, and a specimen is cut out therefrom. Then, using the specimen, the loss tangent of each residue is measured in the same manner as the test method for visco-elasticity of vulcanized rubber under the following conditions to obtain the peak temperature at which the loss tangent becomes maximum.

Initial strain: 10%
Deformation mode: tensile
Frequency: 10 Hz
Semi-amplitude: 1%

Figure 12A:
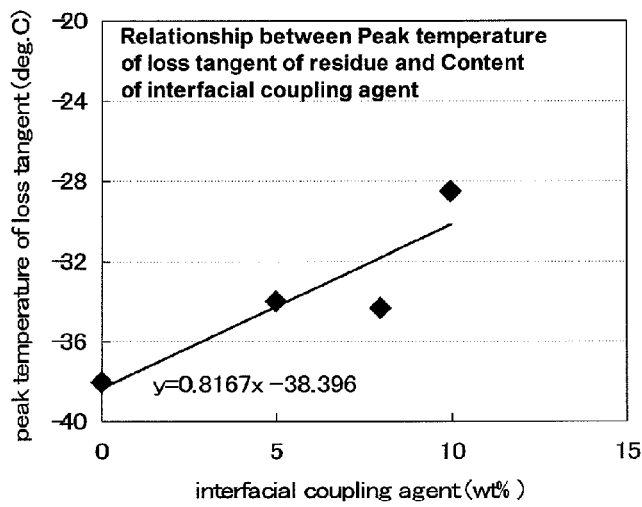

FIG. 12(a) is a graph showing an example of the relationship between the peak temperature of the loss tangent of the residues and the content of the interfacial coupling agent therein.

From the data obtained in the measurement of the peak temperature of the loss tangent, an approximate expression (1) expressing the relationship between the peak temperature and the content of the interfacial coupling agent is obtained by a linear approximation method.

Incidentally, depending on the relationship between the peak temperature and content, a second or higher-degree approximation method may be used as well instead of a linear approximation method.

For example, in the case of FIG. 12(a), the approximate expression (1) is $$y=0.8167x-38.396$$

where y is for the peak temperature, and x is for the content.

In order to increase the accuracy of the approximate expression, it is desirable to use plural kinds of unvulcanized rubber compounds as explained above.

Then, the difference |T2−T1| between the peak temperature T2 of the loss tangent of the second residue without the interfacial coupling agent and the peak temperature T1 of the loss tangent of the first residue with the specific content #Cint of the interfacial coupling agent is estimated using the approximate expression (1).

In the case of FIG. 12(a), the difference |T2−T1| is 6.5336 degrees C. since T1=−31.8624 (=0.8167*8−38.396), T2=−38.396, and T2−T1=−6.5336.

Next, a basic vulcanized rubber compound having a composition same as the composition of the first unvulcanized rubber compound except that silica is removed therefrom is prepared. (sulfur content=#Csul=1 phr)

Also, plural kinds of vulcanized rubber compounds without silica in which the crosslink density is varied from the basic vulcanized rubber compound are prepared by changing the sulfur content. (For convenience sake, the sulfur content is used instead of the crosslink density)

Then, the vulcanized rubber compounds are measured for the peak temperature of the loss tangent as explained above.

Figure 12B:
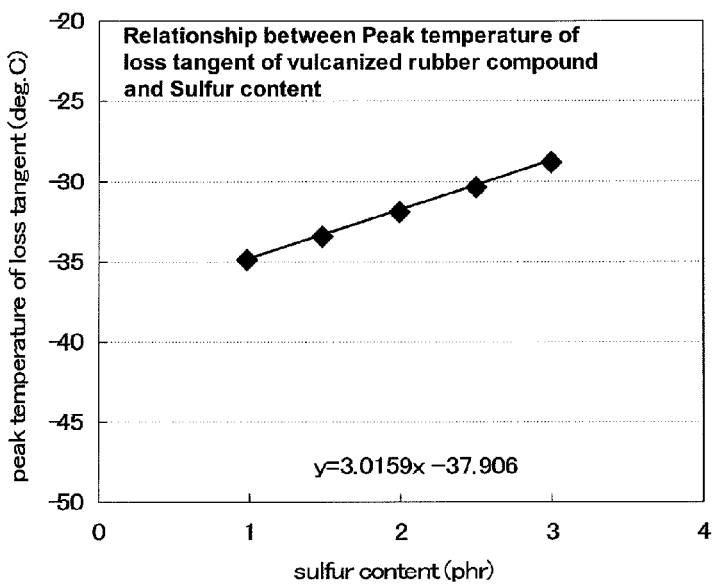

FIG. 12(b) is a graph showing an example of the relationship between the crosslink density (or sulfur content) and the peak temperature of the loss tangent of the vulcanized rubber compounds without silica.

From the data obtained in the experimental measurement of the peak temperature of the loss tangent, an approximate expression (2) expressing the relationship between the peak temperature and the crosslink density (or sulfur content) is obtained by a linear approximation method. As noted above, a second or higher-degree approximation method may be used.

In the example shown in FIG. 12(b), the approximate expression (2) is $$y=3.0159x-37.906$$

where, y is for the peak temperature, and x is for the sulfur content.

Then, using the approximate expression (2), a crosslink density (or sulfur content) when the peak temperature is T3+|T2−T1| is obtained, wherein

|T2−T1| is the above-mentioned difference, and

T3 is the peak temperature when the crosslink density (or sulfur content) is equal to that of the basic vulcanized rubber compound (namely, sulfur content=#Csul=1 phr).

In this example, T3 is −34.8901 degrees C., and

T3+|T2−T1| is −28.3565 degrees C., therefore, the sulfur content at T3+|T2−T1| is 3.17.

Thus, the increase in the peak temperature of the plain vulcanized rubber compound when the sulfur content is increased from #Csul (=1 phr) to a specific value #CsulX (=3.17 phr) is equal to the increase in the peak temperature of the residue when the content of the interfacial coupling agent is increased from 0 to #Cint (=8 wt %).
Therefore, then physical properties of the plain vulcanized rubber whose sulfur content is the specific value #CsulX are experimentally measured and used to define the interface models for example in terms of the stress-elongation relationship.

As explained above, the sulfur content is used as a parameter approximately expressing the crosslink density of the interface model resulting from the interfacial coupling agent. The reason therefor is that, various test results show that the increase in the peak temperature of the loss tangent of the residue due to increase in the interfacial coupling agent content is highly correlative to the increase in the peak temperature of the loss tangent of the plain vulcanized rubber due to increase in the sulfur content.
Accordingly, by defining the parameters of the interface model 23 as explained above, accurate calculation results can be obtained.

Deformation Condition Defining Step S5

In this step S5, deformation conditions are defined in order to deform the rubber compound model 5a.
In the case of the simplified example shown in FIG. 9 and FIG. 11, defined is for example, a condition causing a tensile deformation in the y-direction of the rubber compound model 5a at arbitrary strain rate.

Deformation Simulation Step S6

Figure 13:
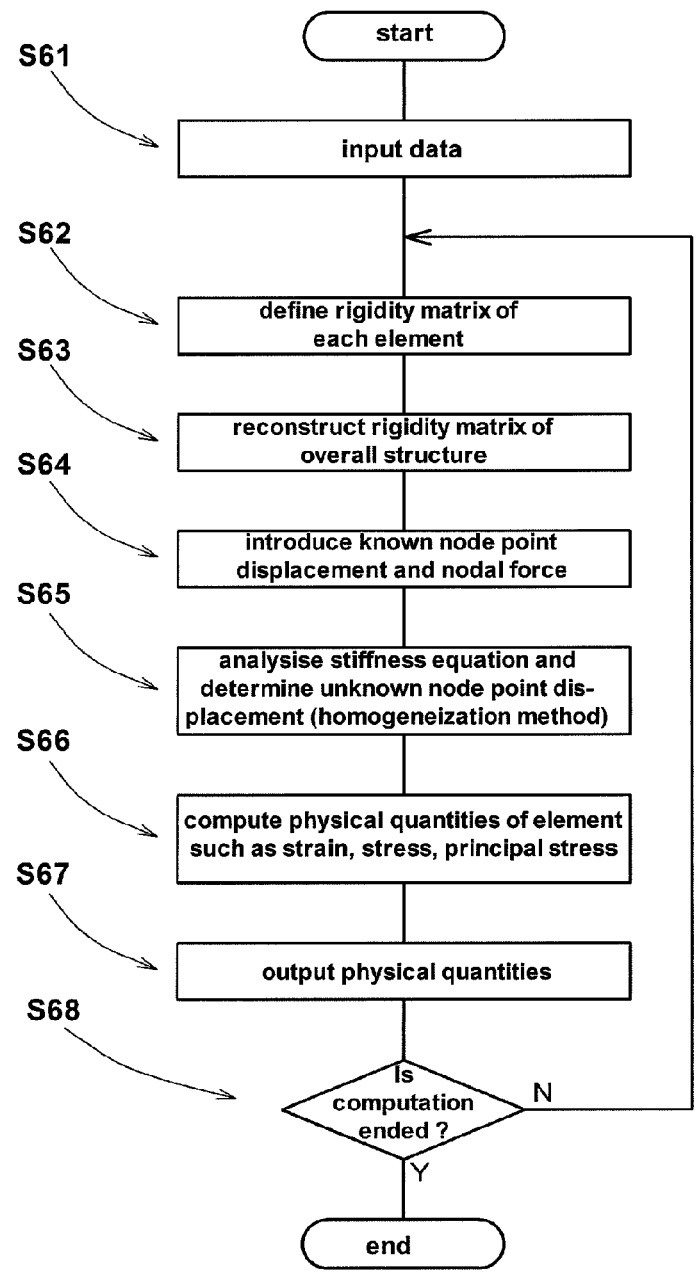
FIG. 13 is a flow chart for explaining a procedure for simulating the deformation.

In this step S6, using the rubber compound model 5a, a deformation simulation is carried out.
FIG. 13 shows a specific example of the procedure of the deformation simulation wherein:—

Firstly, various data of the rubber compound model are input in computer (step S61).
Such data include material characteristics and positions of node points defined for each element.
Based on the input data, the rigidity matrix of each of the elements is defined by the computer (step S62).
Then, the rigidity matrix of the overall structure is reconstructed (step S63).
In the rigidity matrix of the overall structure, the displacement of known node point and nodal force are introduced (step S64).
The stiffness equation is analyzed. Displacement of the unknown node points is determined (step S65).
Physical quantities of each element such as strain, stress, principal stress are computed and outputted (step S66-67).
Then, it is determined whether the computation is to be ended or not (step S68).
If not, step S62 and subsequent steps are repeated.

Such simulation (deformation calculations) can be made by the use of a computer software, for example, an engineering analysis applications software "LS-DYNA" developed by Livermore Software Technology Corporation.

Figure 14:
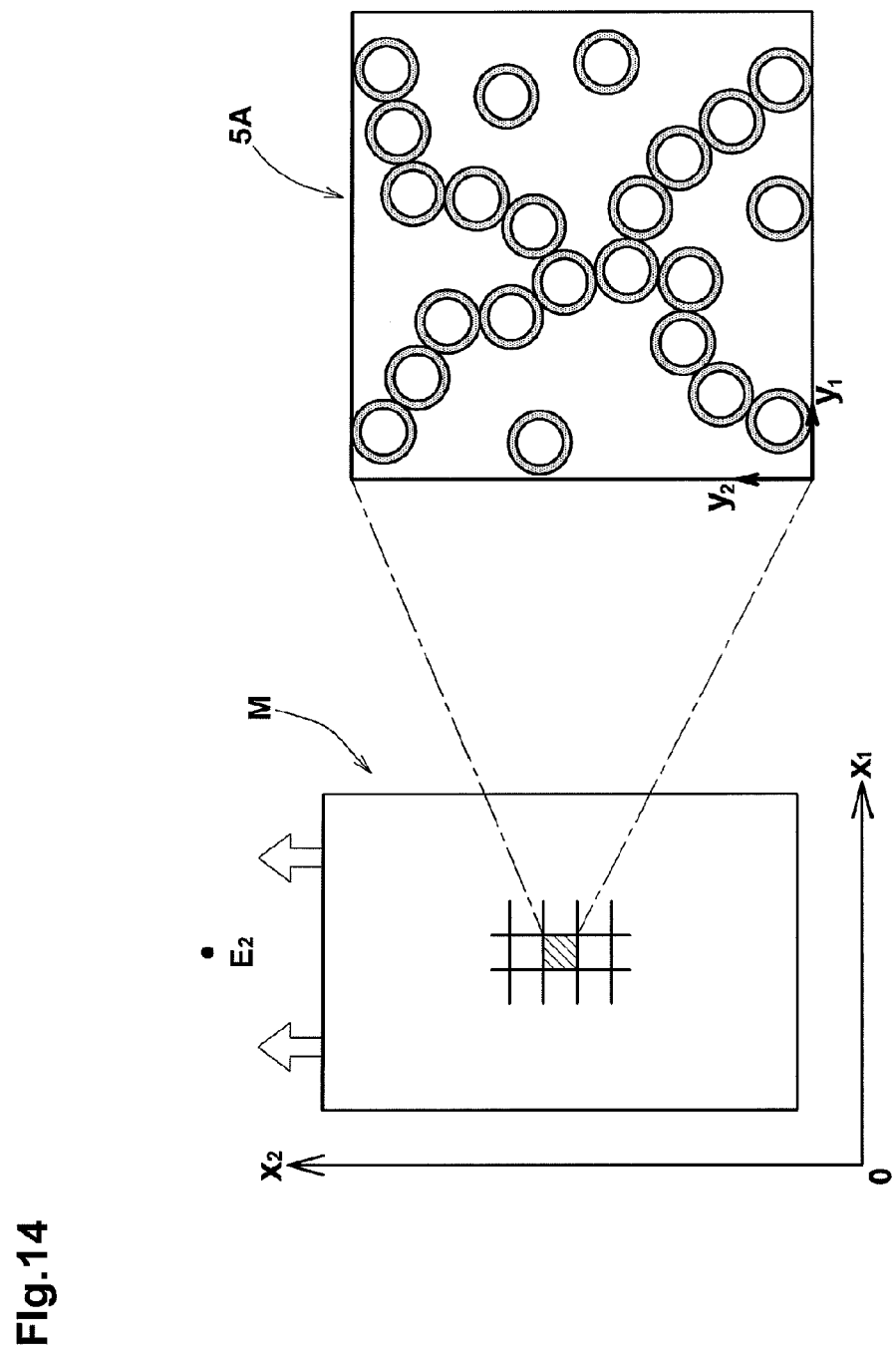
FIG. 14 is a diagram for explaining the relationship between a microscopic structure and the overall structure in a homogenization method.

The simulation is carried out based on a homogeneization method (asymptotic expansion homogeneization method).
In the homogeneization method, as shown in FIG. 14, two independent variables are used.
One is yi representing a microscopic structure (called "unit cell" in the homogeneization method) such as the microscopic structure 5A of the rubber compound model as shown in FIG. 11. The other is xi representing the entirety M of a rubber compound periodically including the microscopic structures.
By making an asymptotic expansion of the independent variable yi in a field of a microscopical scale and the independent variable xi in a field of a macroscopical scale, an average mechanical response of the entirety of the rubber compound in which the model of the microscopic structure as shown in FIG. 11 is reflected can be obtained approximately.

As to the rubber part of the interface models 23 and the rubber component model 21, in order to express a rubber elastic response, it is preferred to make deformation calculations according to a molecular chain network theory known in the art.

Physical Quantity Acquiring Step S7

In this step S7, from the results of the deformation calculations, required physical quantities are acquired.
As to the physical quantities, a stress-strain curve is especially useful for examining the deformational behavior of the silica compounded rubber.
Further, it is possible to visually show a time-series deformation of each element of the rubber compound model, and the distribution of a physical quantity. In this case, it is preferable to color each element according to the magnitude of stress.

By making the simulation using the rubber compound model including the above-mentioned interface models 23, it is possible to accurately simulate the behavior of the interface between the silica particle and the rubber component when an external force is applied, the movements of the silica particles relative to one another and the like. Therefore, it is possible to obtain calculation results more accurate than ever.

Comparison Tests

In order to confirm the advantage of the method according to the invention, comparison tests were conducted.
Firstly, an explanation is given about the STEM image acquiring step S1 and three-dimensional structure reconstruction step S2.

Equipments and materials used are as follows.
Scanning transmission electron microscope: JEOL Ltd. JEM-2100F
Microtome: Leica Ultramicrotome EM UC6
[Rubber Materials]
100 parts by mass of SBR (Sumitomo chemical Company, Limited: SBR1502)
53.2 parts by mass of silica (Rhodia Japan Ltd.: 115Gr)
4.4 parts by mass of interfacial coupling agent (Degussa silane coupling agent Si69)
0.5 parts by mass of sulfur (Tsurumi Chemical. Co. Ltd.: Powdered sulfur)
1 parts by mass of vulcanization accelerator A (Ouchi Shinko Chemical Industrial Co., Ltd.: NOCCELER NS)
1 parts by mass of vulcanization accelerator B (Ouchi Shinko Chemical Industrial Co., Ltd.: NOCCELER D)

Using a banbury mixer, the materials except for the sulfur and vulcanization accelerators were kneaded for four minutes at 160 degrees C. Then, the kneaded materials to which the sulfur and vulcanization accelerators were added was further kneaded by the use of a open roll kneader for two minutes at 100 degrees C., and a raw rubber compound was prepared.
The raw rubber compound was vulcanized for thirty minutes at 175 degrees C.

The vulcanized rubber was sliced by using the ultramicrotome, and a specimen having a thickness of 500 nm was prepared.

Using the STEM mode (camera length L1=150 cm, accelerating voltage=200 kV) of the microscope JEM-2100F, STEM images of the specimen were acquired by changing the tilt angle of the specimen from −60 to +60 degrees at a step of 1 degree, wherein, in the case of test condition 1, the focal point was set at the thickness center of the specimen, and in the case of test condition 2, the focal point was set at the upper surface of the specimen.

From the data of the STEM images obtained under each test condition, a 3D dataset of a three-dimensional structure of the rubber compound was reconstructed.

Figure 15:
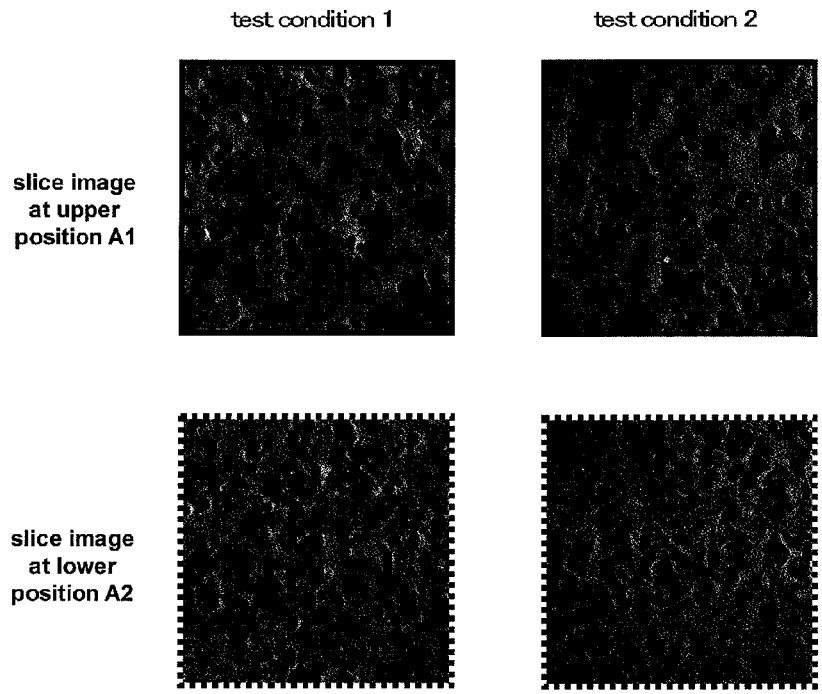
FIG. 15 shows slice images at an upper position and a lower position of a specimen of a rubber compound obtained under the after-mentioned different test conditions 1 and 2.
Figure 16:
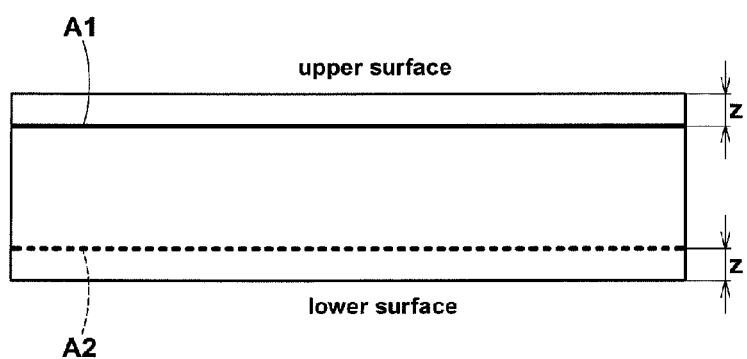
FIG. 16 is a cross sectional view of the specimen for explaining the upper position and lower position referred to in FIG. 15.

FIG. 15 shows slice images at the upper position A1 and lower position A2 of each of three-dimensional structures created from the 3D dataset. The upper and lower positions A1 and A2 are at 40 nm from the upper and lower surfaces, respectively, as shown in FIG. 16.

As shown, in the test condition 2, the image at the lower position became unclear. However, in the test condition 1, the image at the lower position as well as the image at the upper position became clear.

The above-mentioned perspective view shown in FIG. 8 was created from the 3D dataset obtained under the test condition 1.

Based on the slice image at the lower position A2 obtained in the test condition 1, two kinds of two-dimensional rubber compound models (comparative example and embodiment example) made up of square elements were prepared.
In the comparative example, a microscopic structure in the homogeneization method was prepared by dividing a slice image into a rubber component model of square elements and silica particle models of square elements.
In the embodiment example, a microscopic structure in the homogeneization method was prepared, based on the microscopic structure of the comparative example, by further defining 10 nm thickness interface models around the silica particle models.

Then from the microscopic structure, the overall structure was created through a homogeneization method as disclosed in Japanese patent application publication P2010-205165A.

Figure 17:
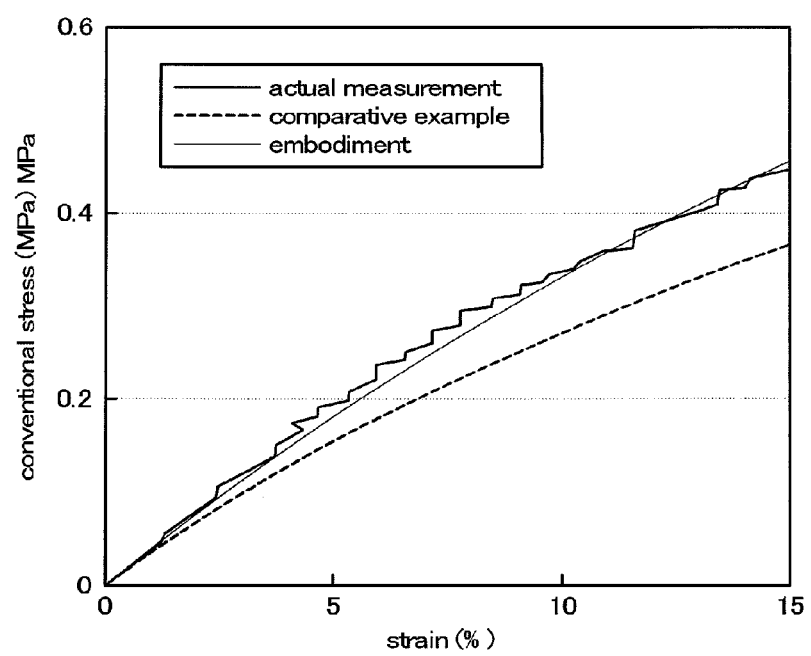
FIG. 17 is a graph showing stress-strain relationships as simulation results and actual measurements.

Using the rubber compound models (embodiment and comparative examples), a simulation for tensile deformation was carried out to obtain the stress-strain relationship under the following conditions.
Maximum tensile strain: 3 mm (maximum strain 15%)
Tensile strain rate: 100 mm/min
Macroscopic region; 20 mm×20 mm The simulation results are shown in FIG. 17 together with the actual measurements obtained from the rubber compound. As shown, the simulation results of the embodiment well coincide with the actual measurements though the simulation results of comparative example have large differences from the actual measurements.

The invention claimed is:

1. A method for simulating deformation of rubber compound including a rubber component, silica particles and an interfacial coupling agent for coupling the silica particles with the rubber component, comprising:
a STEM image acquiring step of acquiring, by the use of a scanning transmission electron microscope (STEM), data of STEM images of the rubber compound;
a three-dimensional structure reconstruction step of reconstructing, based on the data of the STEM images, a dataset of a three-dimensional structure of the rubber compound;
a finite element model generating step of generating, based on the dataset of the three-dimensional structure of the rubber compound, a finite element model of the rubber compound;
a deformation calculation step of making a deformation calculation by the use of the finite element model of the rubber compound on which conditions are defined; and
a step of acquiring a physical quantity through the deformation calculation,
wherein
the finite element model generating step comprises the steps of:
reconstructing data of a slice image of the rubber compound from the dataset of the three-dimensional structure;
identifying a domain of the rubber component and domains of the silica particles in the slice image through an image processing of the slice image; and
generating the finite element model of the rubber compound, wherein the step of generating of the finite element model further comprises the steps of:
creating silica particle models by subdividing the domains of the silica particles into finite elements;
creating an interface model made up of finite elements surrounding each of the silica particle models;
creating a rubber component model by subdividing the domain of the rubber component into finite elements; and
defining a physical property on the finite elements of the interface models as being harder than the rubber component,
wherein the physical property of the interface model is determined by the steps of:
preparing a first unvulcanized rubber compound having the same composition as that of said rubber compound as an analysis object and a second unvulcanized rubber compound having a composition same as the first unvulcanized rubber compound except that the interfacial coupling agent is eliminated;
immersing each of the first and second unvulcanized rubber compounds in solvent to remove the rubber component and thereby to obtain residue;
determining the difference between a peak temperature T1 of a loss tangent of the residue of the first unvulcanized rubber compound and a peak temperature T2 of the loss tangent of the residue of the second unvulcanized rubber compound;
preparing a basic vulcanized rubber compound having a composition same as the first unvulcanized rubber compound except that the silica particles are eliminated, and plural kinds of vulcanized rubber compounds which are the same as the basic vulcanized rubber compound but different in a crosslink density from each other and from the basic vulcanized rubber compound;
measuring a peak temperature of the loss tangent of each of the vulcanized rubber compounds, which are the basic vulcanized rubber compound and said plural kinds of vulcanized rubber compounds;
obtaining, from the measured peak temperature and the crosslink density of each of the vulcanized rubber compounds which are said basic vulcanized rubber compound and said plural kinds of vulcanized rubber compounds, a relationship between the peak temperature of the loss tangent and the crosslink density;
finding, from the obtained relationship, the crosslink density when the peak temperature of the loss tangent is equal to the sum of the difference |T2−T1| and the peak temperature T3 of the loss tangent of the basic vulcanized rubber compound; and measuring the physical property of a vulcanized rubber compound having the found crosslink density and defining the physical property for the interface model.

2. The method according to claim 1, wherein
in the STEM image acquiring step, a focal point of the scanning transmission electron microscope is set in a thickness center region of a specimen of the rubber compound.

3. The method according to claim 1, wherein
in the STEM image acquiring step, a specimen of the rubber compound is tilted with respect to the central axis of the scanning transmission electron microscope, and
the STEM images are took at different tilt angles of the specimen of the rubber compound while a focal point of the scanning transmission electron microscope is set in a thickness center region of the specimen of the rubber compound based on an apparent thickness measured along the direction of an electron beam axis across the specimen of the rubber compound.

4. The method according to claim 1, wherein a thickness of the specimen of the rubber compound is 200 to 1500 nm.

5. The method according to claim 1, wherein
a thickness of the specimen of the rubber compound is 200 to 1500 nm, and
a distance between the specimen of the rubber compound and a detector for the transmission electrons of the scanning transmission electron microscope is 8 to 150 cm.

* * * * *